US010092452B2

(12) United States Patent
Robinson et al.

(10) Patent No.: US 10,092,452 B2
(45) Date of Patent: Oct. 9, 2018

(54) TARGETED DELIVERY OF MAGNETICALLY TAGGED ACTIVE AGENTS IN COMBINATION WITH NEGATIVE PRESSURE WOUND THERAPY

(71) Applicant: KCI Licensing, Inc., San Antonio, TX (US)

(72) Inventors: Timothy Mark Robinson, Basingstoke (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 458 days.

(21) Appl. No.: 14/579,450

(22) Filed: Dec. 22, 2014

(65) Prior Publication Data

US 2015/0112288 A1  Apr. 23, 2015

Related U.S. Application Data

(63) Continuation of application No. 13/323,049, filed on Dec. 12, 2011, now Pat. No. 8,944,067.
(Continued)

(51) Int. Cl.
*A61F 13/00* (2006.01)
*A61M 35/00* (2006.01)
(Continued)

(52) U.S. Cl.
CPC .. *A61F 13/00063* (2013.01); *A61F 13/00068* (2013.01); *A61M 1/0088* (2013.01);
(Continued)

(58) Field of Classification Search
CPC ............ A61K 2300/00; A61K 41/0057; A61K 45/06; A61K 31/198; A61K 31/375;
(Continued)

(56) References Cited

U.S. PATENT DOCUMENTS 1,355,846 A   10/1920   Rannells
2,547,758 A    4/1951   Keeling
(Continued)

FOREIGN PATENT DOCUMENTS

AU    550575 A1    3/1986
AU    745271       4/1999
(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).
(Continued)

*Primary Examiner* — Kim M Lewis (57) ABSTRACT

Methods and systems for treating a wound using targeted delivery of magnetically-tagged active agents in combination with negative pressure wound therapy are presented. In particular, a magnetically-active wound insert may be used to attract magnetically-tagged stem cells to a wound site to treat the wound.

17 Claims, 2 Drawing Sheets

Related U.S. Application Data (60) Provisional application No. 61/423,459, filed on Dec. 15, 2010.

(51) Int. Cl.
  *A61N 1/40* (2006.01)
  *A61M 1/00* (2006.01)
  *A61N 2/06* (2006.01)

(52) U.S. Cl.
  CPC ....... *A61N 1/40* (2013.01); *A61M 2202/0437* (2013.01); *A61N 2/06* (2013.01)

(58) Field of Classification Search
  CPC ...... A61K 33/30; A61K 41/00; A61K 31/282; A61K 41/004; A61K 9/5073; A61K 9/5084; A61K 31/445; A61K 31/714; A61K 31/717; A61B 17/1322; A61B 17/1327; A61B 5/0075; A61B 5/14551; A61B 17/132; A61B 19/00; A61B 19/12; A61B 19/42; A61B 2019/085; A61B 5/14; A61B 5/150839; A61B 17/1325; G01J 2003/2826; G01J 3/0224; G01J 3/0264; G01J 3/0289; G01J 3/28; G01J 3/2823; G01J 3/32; A41D 13/0007; A41D 13/03; A41D 1/08; A61L 29/085; A61L 29/06; A61L 2300/102; A61L 29/16; A61L 2300/104; A61L 2300/206; A61L 2300/404; A61L 2300/606; A61L 2400/10; A61L 29/106; A61L 29/14; A61L 15/28; A61L 15/425; A61L 15/58; A61L 2400/04; A61L 15/24; A61L 15/60; A61L 15/07; C08L 75/04; C08L 67/04; A61F 13/0276; A61F 17/00; A61F 2013/00472; A61F 13/00063; A61F 13/02; A61F 13/0203; A61F 13/10; A01M 31/008; A62B 23/025; A61M 2205/59; A61M 25/02; A61M 5/52; B42C 19/02; B65H 35/08

See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| RE34,866 E * | 2/1995 | Kensey .............. A61B 17/0057 606/213 |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,146,324 A | 11/2000 | Engel |
| 6,174,544 B1 | 1/2001 | Jensen |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |

(56) References Cited

U.S. PATENT DOCUMENTS

| | | | |
|---|---|---|---|
| 2004/0138552 A1* | 7/2004 | Harel | A61B 1/00158 600/407 |
| 2006/0079852 A1 | 4/2006 | Bubb et al. | |
| 2007/0218285 A1 | 9/2007 | Malessa | |
| 2009/0287060 A1* | 11/2009 | Pell | A61B 17/02 600/201 |
| 2010/0030132 A1* | 2/2010 | Niezgoda | A61L 2/035 604/22 |
| 2010/0215708 A1 | 8/2010 | Zumbuehl et al. | |
| 2010/0268176 A1* | 10/2010 | Johnson | A61M 1/0088 604/290 |
| 2014/0257212 A1* | 9/2014 | Boynton | A61M 1/0031 604/319 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0214368 A1 | 3/1987 |
| EP | 0358302 A2 | 3/1990 |
| EP | 0380253 A2 | 8/1990 |
| EP | 1018967 B1 | 8/2004 |
| EP | 1452155 A2 | 9/2004 |
| EP | 2031285 A2 | 3/2009 |
| GB | 692578 | 6/1953 |
| GB | 1122796 A | 8/1968 |
| GB | 1190733 A | 5/1970 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | S60192738 A | 10/1985 |
| JP | 4129536 | 4/1992 |
| SG | 71559 | 3/1999 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2007046806 A1 | 4/2007 |
| WO | 2010093420 A2 | 8/2010 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinović, V. Đukić,Ž Maksimović, Đ. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

(56) References Cited

OTHER PUBLICATIONS

M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

\* cited by examiner

TARGETED DELIVERY OF MAGNETICALLY TAGGED ACTIVE AGENTS IN COMBINATION WITH NEGATIVE PRESSURE WOUND THERAPY

CROSS-REFERENCE TO RELATED APPLICATION

This application is a continuation of U.S. patent application Ser. No. 13/323,049 filed Dec. 12, 2011, which issued as U.S. Pat. No. 8,944,067 on Feb. 3, 2015, which claims priority to U.S. Provisional Patent Application Ser. No. 61/423,459 filed Dec. 15, 2010. This provisional application is expressly incorporated by reference.

BACKGROUND

1. Field of the Invention

The present invention relates generally to healing of wounds and wound-treatment therapies. More particularly, but not by way of limitation, the present invention relates to fluid-instillation and negative-pressure wound therapies.

2. Background Information

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a wound insert (e.g., a porous pad or other manifold device). The wound insert typically contains cells or pores that are capable of distributing reduced pressure to the tissue and channeling fluids that are drawn from the tissue. The wound insert can be incorporated into a wound dressing having other components that facilitate treatment, such as, for example, a drape (e.g., adhesive surgical drape). Instillation fluids may be delivered to the wound insert and held in place at the site of the wound, further improving the efficacy of treatment.

In addition, a technique for magnetically tagging stem cells with an iron-containing clinical agent has recently been developed. See Kyrtatos et al., "Magnetic Tagging Increases Delivery of Circulating Progenitors in Vascular Injury," *JACC Cardiovascular Interventions,* 2009; 2(8); 794 DOI: 10 1016/j.jcin.2009.05.014. Endothelial progenitor cells—a type of cell proven to be important in the vascular healing process—have been tagged with superparamagnetic iron oxide nanoparticles (SPION) and directed to a site of arterial injury using a disc magnet positioned outside the body. SPION has been approved by the U.S. Food and Drug Administration for use in humans, most often to monitor cells in humans using magnetic resonance imaging procedures. Improved delivery and retention of the magnetically-tagged stem cells was observed.

As described herein, it is possible to use magnetically-tagged clinical agents in combination with negative-pressure wound therapy for improved efficacy of wound treatment.

SUMMARY

Wound inserts, and methods for making and using them, are presented. In certain embodiments, a wound-treatment method is presented comprising: obtaining a wound dressing comprising a drape coupled to the skin adjacent a wound of a patient such that the drape covers the wound and forms a space between the drape and the wound and a wound insert disposed within the space wherein the wound dressing is configured to be coupled to a negative pressure source; introducing a magnetically-tagged therapeutic agent into the body of the patient; and applying negative pressure to the wound dressing using the negative pressure source.

In some embodiments, the wound insert further comprises a magnetic material. In some embodiments, the magnetic material may be iron oxide or SPION.

In specific embodiments, the wound insert may comprise a surface and an interior portion. In some embodiments the surface of the wound insert may be coated with the magnetic material, or the magnetic material may be dispersed throughout the interior portion of the wound insert.

Certain embodiments of the method further comprise the step of releasing negative pressure from the wound dressing. Still other embodiments of the method further comprise the step of reapplying negative pressure to remove accumulated fluid from the wound site. And other embodiments may comprise the step of modulating the negative pressure on the wound dressing. Some embodiments further comprise the step of comprising modulating the density of the wound insert.

In some embodiments, the wound dressing comprises an electromagnet configured to be coupled to a voltage source. The strength of the magnetic field generated by the electromagnet may be modulated in some embodiments. The electromagnet may be coupled to the drape adjacent and external to the wound in certain embodiments. In other embodiments, the electromagnet may be disposed within a cuff configured to fit around a limb upon which the wound is located, or the electromagnet may be disposed within a pad.

In some embodiments, the method comprises the step of holding a magnet sufficiently close to the wound that the magnetically-tagged therapeutic agent is drawn toward the wound. The wound insert may be hydrophobic in some embodiments.

In some embodiments, the introducing step further comprises systemically injecting the therapeutic agent. In other embodiments, the introducing step further comprises applying a topical medicament comprising the therapeutic agent. In still other embodiments, the introducing step further comprises spraying the therapeutic agent on the wound. The therapeutic agent may be disposed within the wound dressing in some embodiments. In certain embodiments, the therapeutic agent further magnetic nanoparticles. The magnetic nanoparticles may be SPION in some embodiments. In certain embodiments, the magnetic poles of the magnetic nanoparticles are aligned in a first direction.

In some embodiments, the therapeutic agent may comprises stem cells, a growth factor, a debriding agent, or an antibiotic.

In certain embodiments, a system is presented. In particular, certain embodiments of a wound treatment system may comprise a wound dressing comprising a drape coupled to the skin adjacent a wound of a patient such that the drape covers the wound and forms a space between the drape and the wound; and a wound insert disposed within the space configured to attract a magnetically-tagged therapeutic agent, the wound insert having a surface and an interior portion; and a negative pressure source configured to be coupled to the wound dressing.

In certain embodiments, the wound insert further comprises magnetic particles. The magnetic particles may comprise superparamagnetic iron oxide. In some embodiments, the wound insert may comprise open-celled foam or open-celled reticulated foam.

In some embodiments, the wound insert may comprise a permanent magnet or an electromagnet.

In still other embodiments, a wound insert is presented. In certain embodiments, a wound insert is presented that comprises a foam member comprising an exterior surface and an interior portion; and magnetic particles permanently coupled to the foam member; where the wound insert is configured to be placed in a wound and is further configured to attract magnetically-tagged therapeutic agents. In other specific embodiments, the wound insert comprises a foam member comprising an exterior surface and an interior portion; and a magnet coupled to the foam member; where the wound insert is configured to be placed in a wound and is further configured to attract magnetically-tagged therapeutic agents.

In certain embodiments, the foam member may comprises an open-celled foam or an open-celled reticulated foam.

In some embodiments, the magnetic particles may be coated on the exterior surface of the foam member, disposed within the interior portion of the foam member, or both. The magnetic particles may comprise superparamagnetic iron oxide in some embodiments.

In some embodiments, the wound insert may comprise a polyurethane, such as polyurethane-polyester or polyurethane-polyether; polyolefins, such as polypropylenes (PP) or polyethylenes (PE); silicone polymers; polyvinylchloride; polyamides; polyesters; acrylics; thermoplastic elastomers such as styrene-butene-styrene (SBS) or styrene-ethylene-butene-styrene (SEBS); polyether-amide block copolymers (PEBAX); elastomers such as styrene butadiene rubber (SBR); ethylene propylene rubber (EPR); ethylene propylene diene modified rubber (EPDM); natural rubber (NR); ethylene vinyl acetate (EVA); polyvinyl alcohol (PVOH); polyvinyl acetal; or polyvinyl butyral (PVB); bioabsorbable polymers including polylactic acid, polylactide (PLA), polyglycolic acid, polyglycolide (PGA), and polycaprolactone (PCL).

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DESCRIPTION OF ILLUSTRATIVE EMBODIMENTS

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a wound-treatment method that "comprises," "has," "includes" or "contains" one or more steps possesses those one or more steps, but is not limited to possessing only those one or more steps. Likewise, a wound dressing that "comprises," "has," "includes" or "contains" one or more elements possesses those one or more elements, but is not limited to possessing only those elements. For example, in a wound dressing that comprises one of the present wound inserts and a drape, the wound dressing includes the specified elements but is not limited to having only those elements. For example, such a wound dressing could also include a connection pad configured to be coupled to a negative pressure wound therapy (NPWT) apparatus (e.g., including a vacuum source and/or a fluid source).

Further, a device or structure that is configured in a certain way is configured in at least that way, but it can also be configured in other ways than those specifically described.

Figure 1:
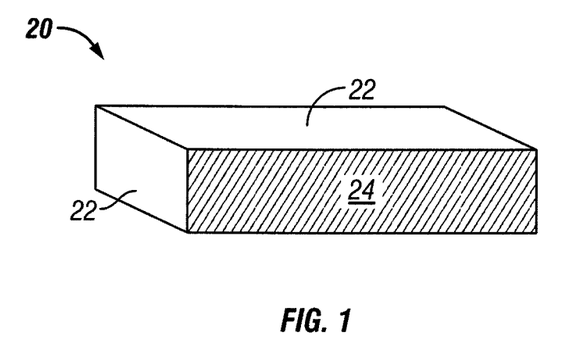
FIG. 1 illustrates an embodiment of a wound insert.
Figure 2:
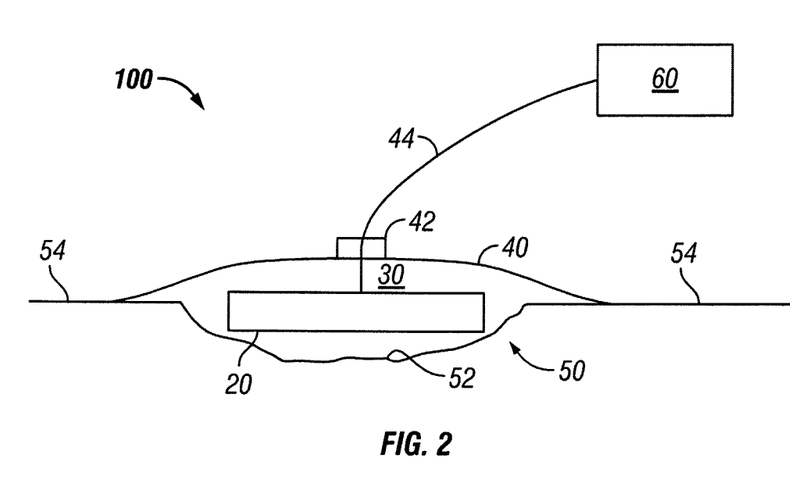
FIG. 2 illustrates an embodiment of a wound treatment system.

Turning now to the figures, FIG. 1 depicts a wound insert 20 that may be used in combination with the wound treatment system 100 shown in FIG. 2. Wound insert 20 may comprise a foam member, which may be open-celled, close-celled, and/or reticulated. In specific embodiments, the wound insert comprises an open-celled reticulated foam. An open-celled reticulated foam has a netlike microstructure, with few if any closed cells. In certain embodiments, the porosity can range from 95%-98%, though less porous or more porous foams may be used.

In certain embodiments, wound insert 20 may comprise a polyurethane, such as polyurethane-polyester or polyurethane-polyether; polyolefins, such as polypropylenes (PP) or polyethylenes (PE); silicone polymers; polyvinylchloride; polyamides; polyesters; acrylics; thermoplastic elastomers such as styrene-butene-styrene (SBS) or styrene-ethylene-butene-styrene (SEBS); polyether-amide block copolymers (PEBAX); elastomers such as styrene butadiene rubber (SBR); ethylene propylene rubber (EPR); ethylene propylene diene modified rubber (EPDM); natural rubber (NR); ethylene vinyl acetate (EVA); polyvinyl alcohol (PVOH); polyvinyl acetal; or polyvinyl butyral (PVB). Additionally, wound insert 20 may comprise a bioabsorbable polymer, examples of which include polylactic acid, polylactide (PLA), polyglycolic acid, polyglycolide (PGA), and polycaprolactone (PCL). Methods of manufacturing open-celled reticulated foam are well known. Open-celled reticulated foam is commercially available from a variety of sources, including Kinetic Concepts, Inc., San Antonio, Tex., <www.kci1.com>, 1-800-275-4524.

Wound insert 20 comprises surfaces 22 and an interior portion 24. Wound insert 20 may be of any suitable shape having a depth dimension, including a sheet, a rectangular prism, a cone, a cylinder, a sphere, or any other suitable shape.

In some embodiments, wound insert 20 is capable of generating a magnetic field. In specific embodiments, super-paramagnetic iron oxide nanoparticles (SPION) are coupled to wound insert 20, although other suitable biocompatible magnetic particles may be used. Wound insert 20 may be spray-coated with SPION such that magnetic nanoparticles are affixed to surfaces 22, and are not disposed within interior portion 24. In other embodiments, surfaces 22 of wound insert 20 may be plasma coated with SPION or other suitable magnetic particles.

In still other embodiments, magnetic particles may be disposed within interior portion 24 of wound insert 20. In one such example, wound insert 20 may be dipped into a slurry comprising SPION or other suitable magnetic particles, allowing the magnetic particles to become bonded or affixed to the cells within interior portion 24 of wound insert 20. The strength of the magnetic field generated by wound insert 20 may be modulated, for example, by changing the density of the wound insert.

In other embodiments, wound insert 20 is configured to be used in conjunction with an electromagnet. In some embodiments, the electromagnet may be located on surface 22 or in interior portion 24 of wound insert 20. In other embodiments, the electromagnet may be located within wound 50, between drape 40 and wound surface 52. In still other embodiments, electromagnet may be placed outside wound 50 and drape 40, such as in a cuff worn by the patient or in a pad placed over drape 40.

In yet other embodiments, wound insert 20 may comprise a macroscopic magnet. For example, a cylindrical magnet, bar magnet, or strip magnet comprising ferromagnetic material may be coupled to a surface 22 of wound insert 20. Or a cylindrical magnet, bar magnet, or strip magnet may be inserted into interior portion 24 of wound insert 20 such that the magnet is disposed within wound insert 20.

Turning now to FIG. 2, wound insert 20 is shown as part of a wound treatment system 100. In the embodiment shown, wound insert 20 is shown placed in wound 50 of a patient (not shown) having a wound surface 52. A drape 40 is placed over wound 50 and wound insert 20 such that wound insert 20 is between drape 40 and wound 50, creating space 30. Drape 40 is coupled to the skin 54 of the patient. Wound insert 20 is coupled to a wound treatment apparatus 60 by conduit 44. Apparatus 60 may comprise a vacuum source configured to apply negative pressure to wound insert 20 through conduit 44. Apparatus 60 may further comprise a fluid source configured to deliver a fluid through conduit 44 to wound insert 20. Examples of such fluids include a medicinal fluids, antibacterial fluids, or irrigation fluids. Various wound therapy systems and components are commercially available through KCI USA, Inc. of San Antonio, Tex., U.S.A.

Conduit 44 can comprise a single lumen conduit (e.g., switched between a vacuum source and/or a fluid source) or can comprise multiple single-lumen conduits or a multi-lumen conduit such that, for example, fluid can be delivered and/or negative pressure can be applied to wound insert 20 individually or simultaneously. Or conduit 44 can comprise multiple lumens, for example, as in a single conduit with a central limit for application of negative pressure and/or fluid delivery and one or more peripheral lumens disposed adjacent or around the central lumen such that the peripheral lumens can be coupled to a pressure sensor to sense and/or detect a pressure or negative pressure between drape 40 and wound surface 52. In the embodiment shown, system 100 further comprises a wound dressing connection pad 42 configured to be coupled (and is shown coupled) to conduit 44. One example of a suitable connection pad 42 is the "V.A.C. T.R.A.C.® Pad," commercially available from KCI USA, Inc. of San Antonio, Tex., U.S.A. One example of a suitable drape 40 includes the "V.A.C.® Drape" commercially available from KCI USA, Inc. (and its affiliates) of San Antonio, Tex., U.S.A.

In the embodiment shown in FIG. 2, apparatus 60 may be configured to deliver instillation fluid to wound 50, to remove fluid from wound 50, and to apply negative pressure to wound 50 through drape 40 and wound insert 20. Together, drape 40 and wound insert 20 may be referred to as a wound dressing 38. A fluid source in apparatus 60 may be activated to deliver fluid, such as saline, to wound surface 52 through conduit 44 coupled to wound insert 20 through connection pad 42. Alternatively, a vacuum source in apparatus 60 may be actuated to provide negative pressure to wound 50 and wound surface 52 through drape 40 and wound insert 20.

Example of instillation fluids that may be delivered to wound 50 are hypochlorous acid (HOCl) and hypochlorite ion (ClO—, which is also commonly referred to, generally understood to be synonymous with, and may be referred to interchangeably in this disclosure as, OCl—), which are examples of effective antimicrobial agents for biocidal action. For example, HOCl is typically capable of killing a broad spectrum of microbes (e.g., fungus, bacteria, viruses, fungus, yeast, and the like); often in a relatively short period of time (e.g., is capable of killing greater than 99% of microbes within a period of less than 10 seconds). Such antimicrobial agents can be generated or formed by a combination of the present reactive agents and fluid (e.g., water and/or aqueous solution, such as, for example, saline solution) and may be more effective and/or more versatile than antibiotics and other commonly used antimicrobial agents used in wound treatment in the past. For example, antibiotics may be bacteria-specific such that testing may be required to determine a suitable antibiotic to use for a specific wound or infection; and/or such that antibiotics may have only limited effectiveness for individual wounds and/or infections (e.g., where testing is not performed and/or where a wound is infected with a plurality of different bacteria). Such testing may take as long as several days to determine an appropriate antibiotic, delaying treatment or selection of an effective antibiotic. Additionally, bacteria may develop resistance to antibiotics, such that antibiotics may have reduced effectiveness after an amount of time. Further, antibiotics are typically administered intravenously (systemically) such that antibiotics may kill beneficial bacteria (e.g., in a patient's digestive system) and/or may cause organ damage (e.g., to a patient's liver).

Further, apparatus 60 may be configured to remove spent instillation fluids, secretions (e.g., pus), and/or infected tissue from wound 50. Undesirable effluent may be removed by actuating the vacuum source in apparatus 60; effluent may flow into wound insert 20, through conduit 44, and into a waste chamber coupled to apparatus 60.

As shown in FIGS. 3A-3D, system 100 may also be configured to deliver magnetically-tagged therapeutic agents through the tissue of the patient to wound surface 52 of wound 50. Similar wound treatment systems 100 are depicted in FIG. 2 and in FIGS. 3A-3D, except that certain elements have been omitted for clarity. Using magnetically-tagged therapeutic agents in combination with negative pressure wound therapy allows for specific targeting of wound sites, maximizing the efficacy of the therapeutic agents while keeping overall dosing low. In addition, the negative pressure wound therapy system may remove any effluent (e.g. excess or by-products of the magnetically-labeled agent and tissues, or any necrotic tissue or excretions).

Figure 3A:
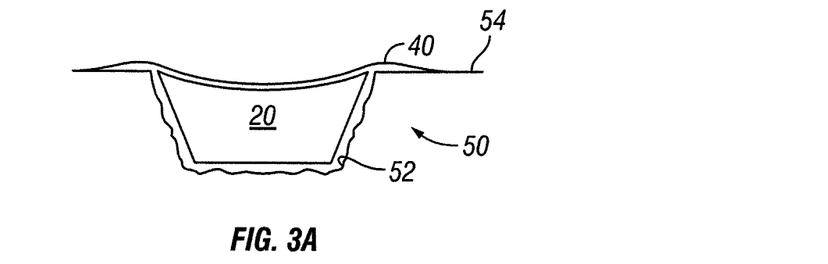
FIGS. 3A-3D illustrate a process for treating a wound with a wound insert and a magnetically-active agent.

As shown in FIG. 3A, wound insert 20 is placed in wound 50 in close contact with wound surface 52. Drape 40 is coupled to skin 54 such that wound insert 20 is between drape 40 and wound surface 52. Negative pressure is applied using a vacuum source in apparatus 60. The negative pressure collapses wound insert 20. In embodiments where wound insert 20 is coated or impregnated with magnetic particles, increasing the density of the wound insert will increase the strength of the magnetic field.

Figure 3B:
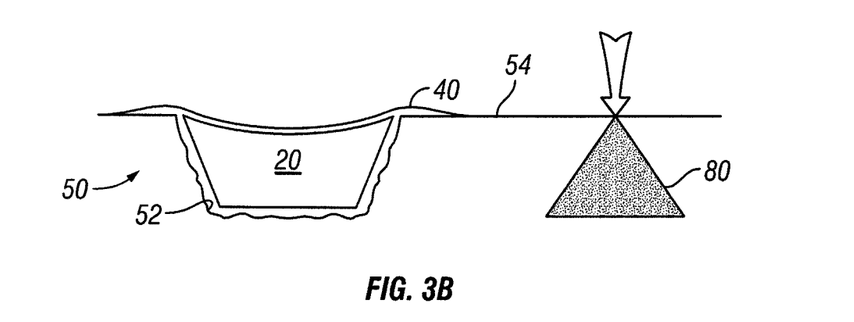

FIG. 3B shows the introduction of therapeutic agent 80 into the body of the patient. Agent 80 may comprise magnetically-tagged stem cells, magnetically-tagged antibiotics, magnetically-tagged debriding agents, or magnetically-tagged growth factors, or any other suitably magnetically-tagged medicament. The magnetic tag may comprise SPION or any other magnetically-active biocompatible nanoparticle. For example, agent 80 may be tagged according to methods disclosed in Kyrtatos et al., "Magnetic Tagging Increases Delivery of Circulating Progenitors in Vascular Injury," *JACC Cardiovascular Interventions,* 2009; 2(8); 794 DOI:10 1016/j.jcin.2009.05.014.

In some embodiments, agent 80 is systemically injected into the patient. Agent 80 can be injected intravenously or into skin 54 near wound 50. In other embodiments, a topical medicament (e.g., a cream) comprising agent 80 is applied to skin 54 near wound 50. In still other embodiments, a bandage or patch comprising agent 80 is placed on skin 54 either separately or as part of the wound dressing.

In other embodiments, agent 80 may be delivered to the wound site via a conduit (e.g., conduit 44) coupled to the wound insert. And in yet other embodiments, agent 80 may be applied directly to wound surface 52 using a spray comprising agent 80, then inserting wound insert 20 and applying drape 40.

Figure 3C:
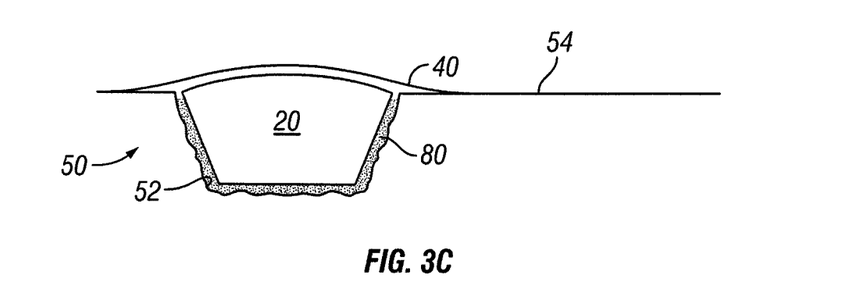

Agent 80 is absorbed into the bloodstream or the lymph and migrates toward wound 50, as shown in FIG. 3C. Agent 80 is drawn to wound insert 20 at the wound boundary between wound surface 52 and wound insert surface 22. Agent 80 may magnetically bond to wound insert 20, which increases the exposure of wound 50 to agent 80. The negative pressure may be released to prevent agent 80 from migrating into interior portion 24 of wound insert 20.

Figure 3D:
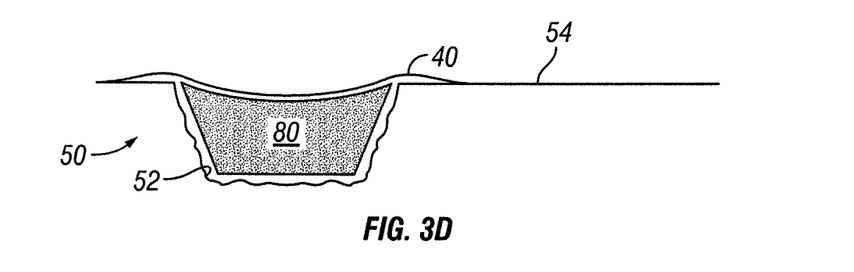

After agent 80 has been exposed to wound 50 for a desired period, negative pressure may once again be reapplied, as shown in FIG. 3D. Agent 80 is drawn into wound insert 20, through conduit 44, and into a waste receptacle coupled to conduit 44. The process may be repeated as required.

In other embodiments, an electromagnet may be used in conjunction with wound insert 20. In these embodiments, the electromagnet may be placed within wound 50, coupled to wound insert 20, coupled to the outside of drape 40 in a pad or cuff, or placed in a wand held near the wound by an operator (e.g., doctor).

The electromagnet may be made to give alternate polarization, such that the magnetically tagged medicaments within agent 80 are made to oscillate. The oscillation of magnetic particles increases their availability to wound surface 52 by ensuring that unused therapeutic agents are available.

In some embodiments, the magnetic particles coupled to the medicaments within agent 80 are uniformly aligned. That is, each medicament (e.g., stem cell, antibiotic, debriding agent, growth factor, etc.) within agent 80 is coupled to a magnetic nanoparticle whose poles are oriented in the same way relative to every other medicament. Such medicament orientation helps magnify the oscillation effect. Also, uniformly-oriented medicaments will aid in delaying the migration of agent 80 into wound insert 20 when negative pressure is applied.

In certain embodiments, arrival of agent 80 at wound 50 results in an increase in the magnetic field present at wound 50, which indicates that the dose has arrived at the wound. The increase in magnetic field may be equated to amount of agent 80 present at the wound site, which may aid in monitoring the dosing received if agent 80 is systematically injected.

In other embodiments, a plurality of electromagnets may be disposed within wound insert 20 or in an external device such as a pad or wand. For example, in one embodiment several electromagnets may be disposed in a pad external and adjacent to a long incisional wound. Agent 80 may be dosed at one end of the wound, and each electromagnet may be turned on and off in sequence to draw agent 80 along the full length of the wound.

In other embodiments, several electromagnets may be disposed within wound insert 20 for deep wounds and therapy such as instillation. In such embodiments, agent 80 may be delivered to the entirety of wound 50, then controlled to exit wound 50 by modulating the strength of the magnetic field generated by the electromagnet.

In still other embodiments, agent 80 may be a magnetically-tagged debriding agent. In such applications, necrotic tissue may be located, and permanent or electromagnets may be placed in the necrotic tissue. The debriding agent may be drawn through wound 50 to these locations only.

The various illustrative embodiments of devices, systems, and methods described herein are not intended to be limited to the particular forms disclosed. Rather, they include all modifications and alternatives falling within the scope of the claims.

The claims are not intended to include, and should not be interpreted to include, means-plus- or step-plus-function limitations, unless such a limitation is explicitly recited in a given claim using the phrase(s) "means for" or "step for," respectively.

We claim:

1. A wound treatment system for use in treating tissue at a wound site in patient, comprising:
    a wound dressing comprising:
        a drape adapted to be coupled to skin adjacent to the wound such that the drape covers the wound and forms a space between the drape and the wound; and
        a wound insert disposed within the space configured to attract a magnetically-tagged therapeutic agent to the tissue and increase exposure of the tissue to the agent, the wound insert comprising a magnetic material; and
    a delivery member configured to provide the magnetically-tagged therapeutic agent.

2. The system of claim 1, where the magnetic material comprises magnetic particles dispersed in the wound insert.

3. The system of claim 2, where the magnetic particles comprise superparamagnetic iron oxide.

4. The system of claim 1, where the wound insert comprises open-celled foam.

5. The system of claim 4, where the wound insert comprises open-celled reticulated foam.

6. The system of claim 1, where the magnetic material comprises a permanent magnet.

7. The system of claim 1, wherein the delivery member is adapted to deliver the magnetically-tagged therapeutic agent to a tissue site adjacent to the wound.

8. The system of claim 1, wherein the delivery member comprises a patch adapted to be applied to a tissue site adjacent to the wound.

9. The system of claim 1, wherein the delivery member is adapted for systemically injecting the magnetically-tagged therapeutic agent into the patient.

10. The system of claim 1, further comprising a negative pressure source configured to be coupled to the wound dressing.

11. A wound treatment system for treatment of a wound, comprising:
- a wound insert adapted to be disposed adjacent to the wound and configured to attract a magnetically-tagged therapeutic agent to the wound so as to increase exposure of the wound to the agent, the wound insert comprising an open-celled foam member and magnetic particles coated on or dispersed in the foam member;
- a negative pressure source;
- a conduit in fluid communication with the negative pressure source, configured to deliver an instillation fluid to the wound, to remove fluid from the wound, and to apply negative pressure to the wound; and
- a delivery member configured to provide the magnetically-tagged therapeutic agent to a site not in the wound.

12. The system of claim 11, wherein the magnetic particles are coated on an exterior surface of the foam member.

13. The system of claim 11, wherein the magnetic particles are disposed within the interior portion of the foam member.

14. The system of claim 11, further comprising a drape coupled to the skin adjacent the wound of a patient such that the drape covers the wound and the wound insert.

15. The system of claim 11, wherein the delivery member comprises a patch adapted to be applied to a tissue site adjacent to the wound.

16. The system of claim 11, wherein the delivery member is adapted for systemically injecting the magnetically-tagged therapeutic agent into the patient.

17. The system of claim 11, wherein the magnetic particles are superparamagnetic iron oxide nanoparticles.

* * * * *